(12) United States Patent
Noguchi et al.

(10) Patent No.: US 12,379,365 B2
(45) Date of Patent: Aug. 5, 2025

(54) EFFECTIVE MATERIAL AGE ESTIMATION DEVICE, COMPRESSIVE STRENGTH ESTIMATION DEVICE, AND PROGRAM

(71) Applicants: THE UNIVERSITY OF TOKYO, Tokyo (JP); JUST.WILL CO., LTD., Fukuoka (JP); Beeinventor Limited, Taipei (TW); E-FUJI COMPANY LTD., New Taipei (TW)

(72) Inventors: Takafumi Noguchi, Tokyo (JP); Bochao Sun, Tokyo (JP); Masahiro Hayasaki, Fukuoka (JP); Shigeyuki Nishijima, Fukuoka (JP); Hideyuki Yamamoto, Fukuoka (JP)

( * ) Notice: Subject to any disclaimer, the term of this patent is extended or adjusted under 35 U.S.C. 154(b) by 245 days.

(21) Appl. No.: 18/003,693

(22) PCT Filed: Oct. 23, 2020

(86) PCT No.: PCT/JP2020/039895
§ 371 (c)(1),
(2) Date: Dec. 29, 2022

(87) PCT Pub. No.: WO2022/003994
PCT Pub. Date: Jan. 6, 2022

(65) Prior Publication Data
US 2023/0258621 A1    Aug. 17, 2023

(30) Foreign Application Priority Data
Jun. 30, 2020    (JP) ................. 2020-113105

(51) Int. Cl.
*G01N 33/38* (2006.01)

(52) U.S. Cl.
CPC ................. *G01N 33/383* (2013.01)

(58) Field of Classification Search
CPC ........ G01N 33/38; G01N 33/383; G01N 3/08; G01N 27/223; G01N 3/405; G01N 3/60;
(Continued)

(56) References Cited

FOREIGN PATENT DOCUMENTS

| CN | 106018761 A | 10/2016 |
| JP | 2006-71575 A | 3/2006 |

(Continued)

*Primary Examiner* — Brandi N Hopkins
(74) *Attorney, Agent, or Firm* — OPES IP Consulting Co., Ltd.

(57) ABSTRACT

Provided is an effective material age estimation device capable of appropriately taking relative humidity variation into consideration when estimating an effective material age. This effective material age estimation device comprises a temperature term calculation unit 13 for calculating a temperature term $\gamma_T$ dependent on the temperature of cast concrete, a humidity term calculation unit 14 for calculating a humidity term $\gamma_{RH}$ dependent on the relative humidity of the concrete, and an effective material age calculation unit 15 for calculating the effective material age of the concrete by summing products of the temperature term $\gamma_T$, the humidity term, and a step time term $\Delta t_i$. The humidity term $\gamma_{RH}$ is introduced, and the sum of the products is weighted using the term.

8 Claims, 5 Drawing Sheets

(58) Field of Classification Search
CPC .......... G01N 25/20; G01N 25/00; G01N 3/24;
G01N 5/04; G01N 11/00; G01N 22/00;
G06F 30/20; G06F 30/23; G06F 30/13;
E21D 11/10; B28B 7/42; E02D 29/04;
E04G 21/10
See application file for complete search history.

(56) References Cited

FOREIGN PATENT DOCUMENTS

| | | | | |
|---|---|---|---|---|
| JP | 2008-224649 | A | 9/2008 | |
| JP | 2013-244625 | A | 12/2013 | |
| JP | 2014-35629 | A | 2/2014 | |
| JP | 2014-77241 | A | 5/2014 | |
| JP | 2015-10918 | A | 1/2015 | |
| JP | 2016-37014 | A | 3/2016 | |
| JP | 6050046 | B2 | 12/2016 | |
| JP | 6553347 | B2 | 7/2019 | |
| WO | WO-2020210861 | A1 * | 10/2020 | ............... G01C 9/00 |

* cited by examiner

EFFECTIVE MATERIAL AGE ESTIMATION DEVICE, COMPRESSIVE STRENGTH ESTIMATION DEVICE, AND PROGRAM

CROSS-REFERENCE TO RELATED APPLICATIONS

This application claims priority of Japan Patent Application No. 2020113105, filed on Jun. 30, 2020, the content of which is incorporated herein in its entirety by reference.

PRIOR ART

Reference 1: Japanese registered patent No. 6050046;
Reference 2: Japanese registered patent No. 6553347;
Reference 3: Japanese application Laid-open No. H11-271301;
Reference 4: Japanese application Laid-open No. 2003-279512; and
Reference 5: Japanese application Laid-open No. 2011-256061.

BACKGROUND OF THE INVENTION

Field of the Invention

The present invention relates to an effective material age estimation device wherein a humidity term is newly introduced to be estimated in addition to a temperature term upon estimating effective material age and compressive strength of cast concrete so as to be capable of performing appropriate estimation, and art related to the effective material age estimation device.

Description of the Related Art

For example, as recited in Reference 2 (Japanese registered patent No. 6553347), Reference 3 (Japanese application Laid-open No. H11-271301), Reference 4 (Japanese application Laid-open No. 2003-279512), and Reference 5 (Japanese application Laid-open No. 2011-256061), in order to estimate effective material age of cast concrete, there is a known prior art of summing products of a temperature term $\gamma_T$ and a step time term $\Delta t_i$.

In the prior art as described later in detail, it is, however, neglected that relative humidity has a strong influence during strength-increasing process of the cast concrete, particularly in early age of curing thereof. As a result, according to the prior art, the effective material age is overestimated, and appropriate estimation is difficult. Furthermore, there is a serious deficiency in the prior art since the prior art estimates the effective material age toward the opposite side of safe side.

SUMMARY OF THE INVENTION

In view of the above, an object of the present invention is to provide an effective material age estimation device and a compressive strength estimation device both of which can appropriately reflect variation of relative humidity on estimation of the effective material age and the compressive strength.

A first aspect of the present invention provides an effective material age estimation device, comprising: a temperature term calculation unit operable to calculate a temperature term dependent on temperature of cast concrete; a humidity term calculation unit operable to calculate a humidity term dependent on relative humidity of the cast concrete; and an effective material age calculation unit operable to sum products of the temperature term, the humidity term, and a step time term to calculate an effective material age of the cast concrete.

According to this structure, not first products of a temperature term and a step time term but second products of the temperature term, a humidity term, and the step time term are summed. In short, the second products are weighted by means of the humidity term. For example, if the humidity has a value of zero, the second products at the current step time must have the value of zero regardless of the value of the temperature term. In this way, the variation of the relative humidity has appropriate influence on the calculated effective material age. In addition, the humidity term acts in a direction wherein the calculated effective material age is underestimated. In other words, this structure makes it possible to avoid the overestimation that is inevitable according to the prior art as discussed above.

In addition to the first aspect of the present invention, a second aspect of the present invention provides an effective material age estimation device, further comprising a temperature/humidity sensor operable to measure the temperature of the cast concrete and the relative humidity of the cast concrete.

This structure enables to actually measure temperature and relative humidity of the cast concrete to make it possible to perform appropriate calculation based on the actual measured values.

In addition to the first aspect of the present invention, a third aspect of the present invention provides an effective material age estimation device, further comprising a cast concrete detection sensor operable to detect whether or not the cast concrete exists.

According to this structure, calculation with respect to effective material age can be stopped until the cast concrete detection sensor detects that the cast concrete exists. The device can be surely used in a reasonable manner. Especially, wasteful power consumption of the device can be suppressed.

In addition to the first aspect of the present invention, a fourth aspect of the present invention provides an effective material age estimation device, wherein: a predetermined threshold with respect to the relative humidity is set up to be less than 100% and greater than 0%; the humidity term reaches a positive maximum when the relative humidity is 100%; the humidity term decreases within a first range wherein the relative humidity is less than 100% and not less than the predetermined threshold; and the humidity term approaches asymptotically to 0% within a second range wherein the relative humidity is less the predetermined threshold.

This structure enables to set up the humidity term in a manner that matches to an entity.

In addition to the fourth aspect of the present invention, a fifth aspect of the present invention provides an effective material age estimation device, wherein the humidity term is set up to be zero within the second range.

According to this structure, the products always have a value of zero within the second range regardless to the value of the temperature term. Overestimation of effective material age can be suitably avoided.

Herein, in the first through fourth aspects of the present invention, a fifth aspect of the present invention provides to perform calculation as follows.

That is, the temperature term $\gamma_T$ dependent on the temperature of T ° C. is preferably calculated in accordance with (Formula 1):

$$\gamma_T = \exp\left(13.65 - \frac{4000}{273+T}\right).$$

The humidity term $\gamma_{RH}$ dependent on the relative humidity of RH % is preferably calculated in accordance with (Formula 2):

$$\gamma_{RH} = \exp\{-0.8484(100-RH)\}$$

And, the effective material age $t_e$ dependent on the step time term $\Delta t_i$, is preferably calculated in accordance with (Formula 3):

$$t_e = \sum_i \Delta t_i \cdot \gamma_T \cdot \gamma_{RH}.$$

According to this structure, the temperature term $\gamma_T$ and the humidity term $\gamma_{RH}$ are set up by means of suitable exponential functions to be capable of appropriately estimating the effective material age.

In addition to the first aspect of the present invention, a sixth aspect of the present invention provides an effective material age estimation device, wherein the effective material age calculation unit omits to sum the products of the temperature term, the humidity term, and the step time term when the relative humidity is less than the predetermined threshold.

According to this structure, wasteful summing calculation is omitted when it is known that the products have almost exactly a value of zero. It is ensured that the device is used in a reasonable manner. In particular, wasteful power consumption can be suppressed.

In addition to the first aspect of the present invention, a seventh aspect of the present invention provides an effective material age estimation device, wherein the predetermined threshold is set up to be relative humidity from 80% to 95%.

This structure enables to set up the predetermined threshold in a manner that matches to an entity.

In addition to the effective material age estimation device according to the first aspect of the present invention, an eighth aspect of the present invention provides a compressive strength estimation device, comprising a compressive strength calculation unit operable to calculate compressive strength of the cast concrete based on the effective material age.

In addition to the eighth aspect of the present invention, a ninth aspect of the present invention provides a compressive strength estimation device, wherein: the compressive strength is calculated in accordance with at least one of following Formula 4 and Formula 5.

The Formula 4 dependent on the constant s, the setting time $t_s$, and the nominal strength $f_{c28}$ of the cast concrete preferably is:

$$f_{Ct} = \exp\left\{s\cdot\left(1 - \sqrt{\frac{28}{t_e - t_s}}\right)\right\} \cdot f_{c28};$$

and
the Formula 5 dependent on the constants of "a" and "b" preferably is:

$$f_{Ct} = \{t_e/(a+bt_e)\} \cdot f_{c28}$$

Herein, the constant s is calculated based on values recited in the Mill Test Report, or the like. The setting time $t_s$ and the nominal strength $f_{c28}$ have known values recited in the Mill Test Report. For example, the constant a=4.0, and the constant b=0.85 in (Formula 5).

According to this structure, the compressive strength is calculated by means of suitable exponential functions, thereby enabling to estimate the compressive strength with high accuracy.

Effect of Invention

According to the present invention, the humidity term is introduced as discussed above to be added to objects of the products. In other words, the value of products is weighted using the humidity term. In this way, effect of relative humidity can suitably influence the calculated effective material age. The overestimation toward danger side that is inevitable according to the prior art can be appropriately avoided.

In short, the effective material age obtained according to the present invention is estimated toward safe side, and must be said that has high reliability. Furthermore, since the estimated compressive strength is also based on the estimated effective material age with high reliability, the reliability of the estimated compressive strength is also improved in the same way.

DETAILED DESCRIPTION OF THE INVENTION

Prior to concrete explanation of Embodiments, important concepts with respect to the present invention will now be described.

Relative humidity (RH)

Relative humidity indicates a ratio of partial water vapor pressure to saturation vapor pressure at the same temperature T, and is normally expressed as a percentage (%).

If "e" is partial water vapor pressure and "es (T)" is saturation vapor pressure at the same temperature T, then relative humidity RH (%) is expressed by $$RH(\%) = (e/es(T)) * 100(\%).$$

Specific Electrical Resistance

Specific electrical resistance has the same meaning as electrical resistivity and/or resistivity, is a material property indicating how strongly the material resists electric current, and has the unit of [Ωm]

Temperature Term $\gamma_T$ Regarding Effective Material Age

The temperature term $\gamma_T$ regarding effective material age reflects acceleration and/or delay of reaction rate caused by temperature to the material age in accordance with the Arrhenius law. It is assumed that the reference reaction rate is reaction rate of concrete at 20° C., and further that activation energy thereof is 4000. Herein, the temperature term $\gamma_T$ regarding effective material age can be shown in (Formula 1) by means of the temperature T ° C.

Humidity Term $\gamma_{RH}$ Regarding Effective Material Age

The humidity term is a term dependent on the relative humidity RH %. As mentioned in the Description of the Related Art, it is, in the prior art, assumed that the relative humidity is always 100%, and the humidity term has been excluded from consideration. However, at an actual construction site, formworks are removed, the surface of cast concrete is exposed to the outside, and water vapor is released from the surface to the air. In this way, the relative humidity is often less than 100%.

Figure 1:
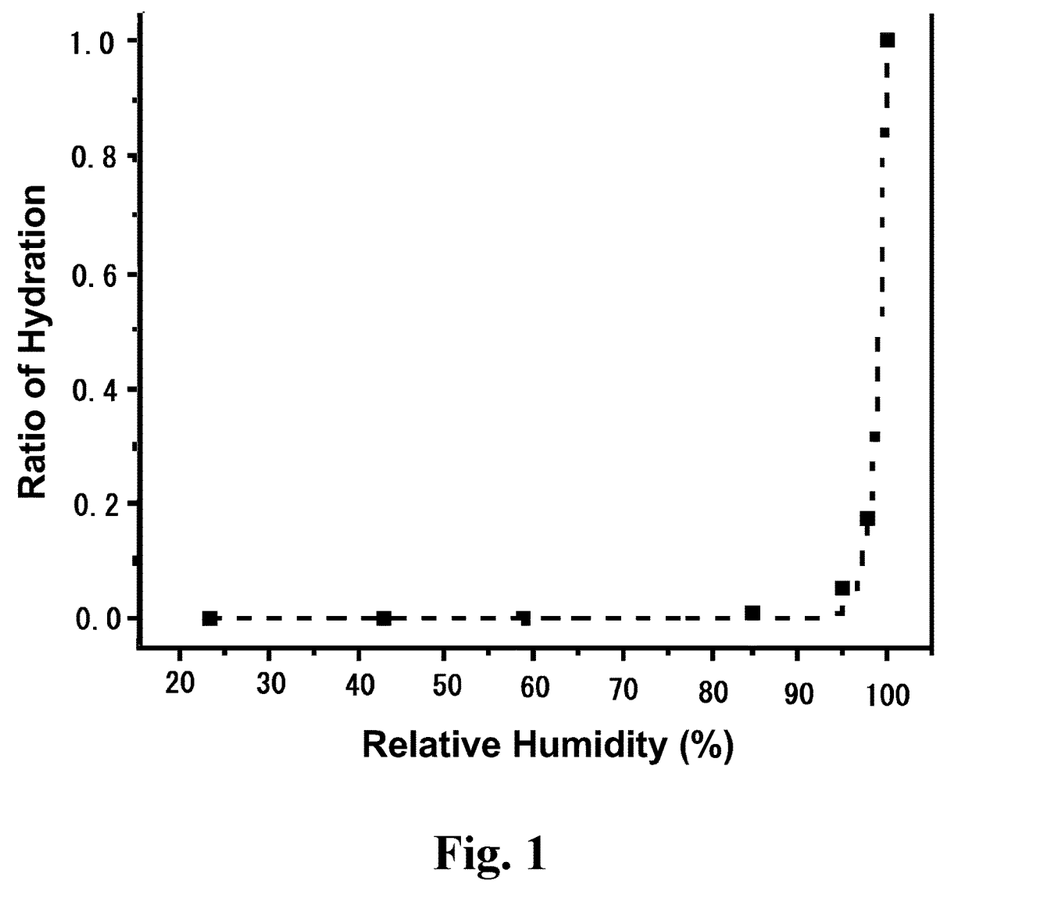
FIG. 1 is a graph showing variation of ratio of hydration.

FIG. 1 is a graph showing variation of the ratio of hydration (dimensionless quantity from 0.0 to 1.0) on the vertical axis with respect to the relative humidity % (from 0 to 100%) on the horizontal axis.

As shown in FIG. 1, the ratio of hydration reaches to be a maximum value of 1.0 when the relative humidity is 100%. On the contrary, when the relative humidity is less than 80%, the ratio of hydration is nearly to be zero, and it can be said that hydration reaction stops virtually.

Accordingly, when only the temperature term is taken into consideration as the prior art, the effective material age is estimated to an opposed side of the safe side, especially if the relative humidity RH is less than 100%. In other words, it can be said that the prior art overestimates the effective material age to the dangerous side, and further that the prior art has a serious fault in this point. More concretely in this Embodiment, the humidity term is calculated in accordance with (Formula 2).

In this Embodiment, relative humidity RH % is directly measured by means of a temperature/humidity sensor S2 (See, FIG. 2.) as described later. The humidity term related to the present invention in this specification, however, has a broader meaning than what is generally recognized, is not limited to what is based on relative humidity directly measured.

For example, as obvious to those skilled in the art, the specific electrical resistance (See, the definition thereof above.) may be obtained using an instrument provided with 4 terminals, and the humidity term dependent on the specific resistance may be used. Otherwise, the water content may be obtained to use another kind of humidity term dependent on the obtained water content. In short, it is sufficient that the humidity term depends directly or indirectly on humidity.

Effective Material Age

In this Embodiment, based on the temperature term $\gamma_T$ and the humidity term $\gamma_{RH}$ calculated as described above, the effective material age is calculated in accordance with (Formula 3).

Compressive Strength

Furthermore in this Embodiment, based on the effective material age calculated as described above, the compressive strength is calculated in accordance with at least one of: (Formula 4) and (Formula 5).

Next, Embodiments of the present invention will now be described with reference to the drawings.

Embodiment 1

Figure 2:
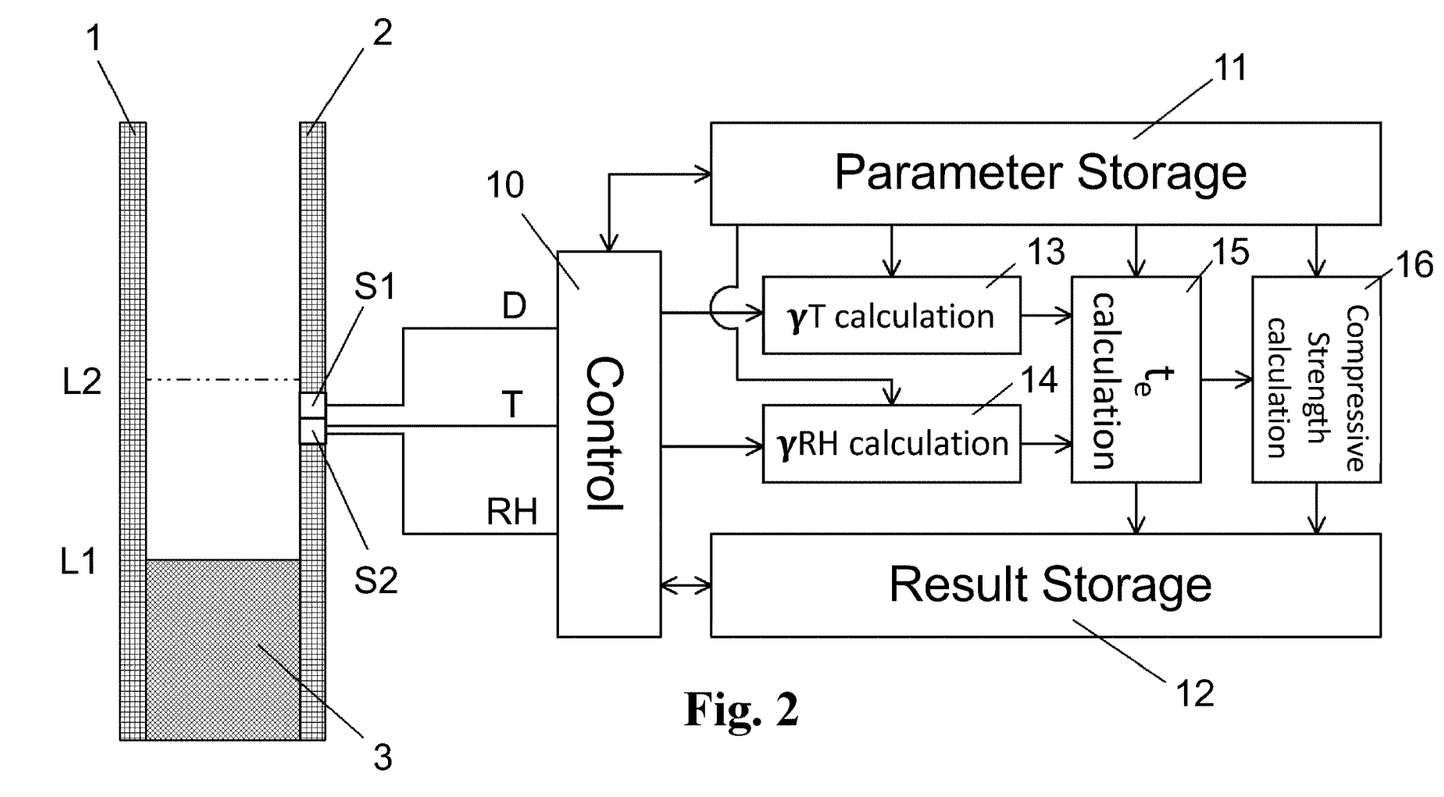
FIG. 2 is a block diagram showing a compressive strength estimation device in Embodiment 1 according to the present invention.
Figure 3:
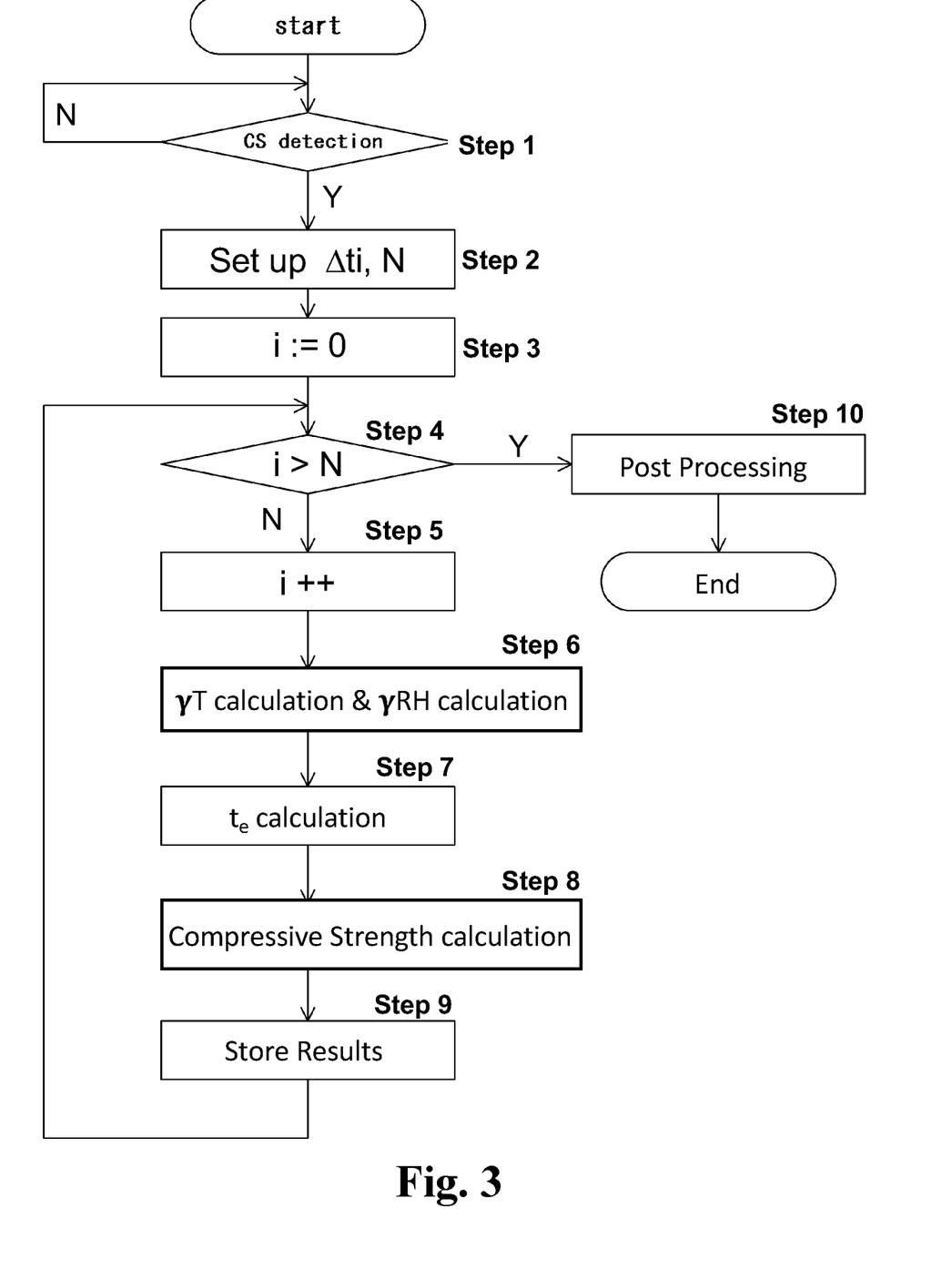
FIG. 3 is a flow chart of the compressive strength estimation device in Embodiment 1 according to the present invention.

FIG. 2 is a block diagram showing a compressive strength estimation device in Embodiment 1 according to the present invention, and FIG. 3 is a flow chart of the same compressive strength estimation device.

As shown in FIG. 2, this example deals with a first case where concrete is cast to construct a part that stands up vertically, for example, a wall and/or a column. As obvious to those skilled in the art, the present invention, however, can also be applied to a second case where a horizontal slab constituting a ceiling and/or a floor is constructed.

As shown in FIG. 2, in this example, a pair of a first formwork 1 and a second formwork 2 are retained so as to stand up while facing to each other with a fixed space. Since timbering, reinforcement members, and/or the like are/is not related to essence of the present invention, illustrations thereof are omitted.

In this example, since the pair of the first formwork 1 and the second formwork 2 stand up vertically, concrete 3 is cast downward from an upper side. In the current state, the first level L1 is equal to a top surface of the cast concrete 3. A cast concrete detection sensor S1 and a temperature/humidity sensor S2 are arranged at a predetermined level of the second formwork 2.

In FIG. 2, although the cast concrete detection sensor S1 is shown higher than the temperature/humidity sensor S2, this arrangement is only for convenience of illustration. It is originally preferable that both of the cast concrete detection sensor S1 and the temperature/humidity sensor S2 are arranged at the same level.

Herein, the cast concrete detection sensor S1 detects whether or not the cast concrete exists near the cast concrete detection sensor S1. The sensor by means of electrostatic capacitance proposed by the present inventors in Reference 1 (Japanese registered patent No. 6050046) can be preferably used as the cast concrete detection sensor S1. Herein, when the top surface of the cast concrete 3 exists at the first level L1 shown with a solid line in FIG. 2, the cast concrete detection sensor S1 has not detected the cast concrete yet, and the cast concrete detection signals indicate OFF. After that, when the casting process proceeds and the top surface of the cast concrete 3 reaches the second level L2 shown with a virtual line in FIG. 2, the cast concrete detection sensor S1 detects the cast concrete to change the cast concrete detection signals to be ON.

The temperature/humidity sensor S2 measures temperature and relative humidity of the cast concrete 3. As the same, a sensor protected by a special film that allows humidity to pass through and further that does not allow water to pass there-through can be preferably used. Needless to say, as the temperature/humidity sensor S2 may be composed of a temperature sensor and a humidity sensor which are separately configured from each other.

The temperature/humidity sensor S2 may be attached with the second formwork 2 as shown in FIG. 2, may be mounted on the cast concrete 3, or may be embedded in the cast concrete 3. Upon embedding the temperature/humidity sensor S2 in the cast concrete 3, it is preferable to embed the same within a surface portion (inside of the covering concrete) that is near to the outside from a reinforcement (not shown). Regardless of arrangement of the same, the temperature/humidity sensor S2 outputs measured temperature signals T and measured relative humidity signals RH after the cast concrete detection signals D have been turned ON.

Among the respective blocks shown in FIG. 2, a portion excluding a compressive strength calculation unit 16 corresponds to an effective material age estimation device in this Embodiment according to the present invention. And, if the compressive strength calculation unit 16 is added to the portion, then a compressive strength estimation device in this Embodiment according to the present invention is constituted as a whole.

Hereinafter, the respective elements will now be explained. First, a control unit 10 is composed of a processor, a memory, or the like (not shown), and controls the entire elements of the compressive strength estimation device. The control unit 10 inputs the cast concrete detection signals D from the cast concrete detection sensor S1, and inputs the temperature signals T and the relative humidity signals RH from the temperature/humidity sensor S2.

A parameter storage unit 11 is composed of a memory (not shown), and stores the respective parameters necessary for calculation process. Especially, the parameter storage unit 11 stores the constant s, the setting time $t_s$, the nominal strength of concrete $f_{c28}$, the step time term $\Delta t_i$, or the like.

A result storage unit 12 is composed of a memory (not shown), and stores the respective values obtained by the calculation process. Especially, the result storage unit 12 stores a counter value i, a process number value N, effective material age $t_e$, compressive strength $f_{cr}$, or the like.

In addition, a temperature term calculation unit 13, a humidity term calculation unit 14, an effective material age calculation unit 15, and a compressive strength calculation unit 16 are the respective modules that perform the respective calculation in response to instructions from the control unit 10.

Herein, needless to say, the respective "calculation unit" in the specification includes a unit that perform direct calculation in accordance with a Formula by means of an argument. However, in addition to this form, the "calculation unit" may have one of various forms other than that, may have a table with an argument as an index, and may determine an intermediated value between two indexes by determining an output value according to proportional distribution.

The temperature term calculation unit 13 inputs the temperature signals T from the control unit 10 to perform calculation in accordance with (Formula 1).

The humidity term calculation unit 14 inputs the relative humidity signals RH from the control unit 10 to perform calculation in accordance with (Formula 2).

The effective material age calculation unit 15 inputs the temperature term $\gamma_T$ from the temperature term calculation unit 13, inputs the humidity term $\gamma_{RH}$ from the humidity term calculation unit 14, inputs the step time term $\Delta t_i$ from the parameter storage unit 11, and sums the products of the inputted terms in accordance with (Formula 3) to store calculation results onto the result storage unit 12.

The compressive strength calculation unit 16 inputs an effective material age from the effective material age calculation unit 15, inputs the constant s, the setting time $t_s$, the nominal strength of concrete $f_{c28}$, or the like from the parameter storage unit 11, and calculate compressive strength in accordance with at least one of: (Formula 4); and (Formula 5) to store calculation results onto the result storage unit 12.

Next, referring to FIG. 3, the flow of processing in the Embodiment 1 will now be explained. First, at Step 1, the control unit 10 waits until the cast concrete detection signals D are turned ON. As long as the control unit 10 waits, the respective calculation units 13-16 do not operate in order to prevent from wasteful power consumption.

When the cast concrete exists at the first level L1 shown in FIG. 2, the cast concrete detection signals D are OFF, and the control unit 10 keeps waiting. After that, when the concrete has been casted continuously to reach the second level L2, the cast concrete detection signals D are turned ON, and the control unit 10 moves the current process to Step 2.

At Step 2, the control unit 10 sets up the step time term $\Delta t_i$ and the number N to store them onto the parameter storage unit 11. The curing period may be various (for example, three days, seven days, 28 days, or the like.) according to a portion wherein the concrete 3 is cast. It is appropriate to set up the step time term $\Delta t_i$ to be about one hour in order to reflect daily temperature variation on calculation results. Needless to say, the step time term $\Delta t_i$ may be set up more finely so as to improve calculation accuracy.

Next at Step 3, the control unit 10 resets the counter i to be zero, and moves the current process to Step 4. At Step 4, the control unit 10 compares the counter i with the number N. If the counter i exceeds the number N, the control unit 10 performs post-processing (for example, writing out various values stored onto the result storage unit 12 to an external storage medium, a predetermined Internet site, or the like.), and then the process will be ended.

Next at Step 4, if the counter i is not greater than the number N, then the control unit 10 increments the counter i, and instructs the temperature term calculation unit 13 and the humidity term calculation unit 14 to perform calculation, respectively.

At Step 7, the temperature calculation unit 13 outputs the temperature term $\gamma_T$, and the humidity term calculation unit 14 outputs the humidity term $\gamma_{RH}$, to the effective material age calculation unit 15, respectively. The effective material age calculation unit 15 obtains effective material age to store the same onto the result storage unit 12, and outputs the same to the compressive strength calculation unit 16.

At Step 8, the compressive strength calculation unit 16 obtains the compressive strength to store the same onto the result storage unit 12 (Step 9), and the current process returns to Step 4.

At Step 4, the control unit 10 performs judgment in the same manner as described above, as long as the current process does not move to Step 10, process from Step 5 to Step 9 is repeated.

Embodiment 2

In the Embodiment 1 as discussed above, summing the products is repeated regardless of the contents of the humidity term. On the contrary in Embodiment 2 as mentioned below, a predetermined threshold TH is newly introduced to perform more reasonable process.

Referring to FIG. 1, it can be understood that the predetermined threshold TH should be set up such that it is less than 100% and greater than 0%.

As shown in FIG. 1, ratio of hydration reaches a positive maximum of 1.0 when the relative humidity is 100%, and decreases within a first range wherein the relative humidity is less than 100% and not less than the predetermined threshold TH, and approaches asymptotically to 0% within a second range wherein the relative humidity is less the predetermined threshold TH.

In view of the above, it may be appropriate that the predetermined threshold TH is set up within a range from 80% to 95%.

Furthermore, sufficient accuracy can be expected for practical use if the humidity term is set to be zero within the second range where the relative humidity is from 0% to the predetermined threshold value TH. Process can be simpler, since the value of products is always to be zero regardless of the value of the temperature term $\gamma_T$. Furthermore in order to make process further simpler, it is practically sufficient to linearly approximate the first range wherein the relative humidity is from 100% to the predetermined threshold value TH, and in this case it is preferable to use a straight line that passes through a point where the relative humidity is 100% and the humidity term is 1.0 (100%) and further that approximates the curve in FIG. 1. It is more preferable that the straight line is set up so as to make the humidity term less than the curve in FIG. 1. This is because the value of the products is set to the safer side as a result. The linear approximation may be performed by a least squares method that is obvious to those skilled in the art.

A basic concept is as mentioned above. In Embodiment 2 dissimilar to Embodiment 1, the predetermined threshold TH is set up within a range from 80% to 95% (more preferably TH=90%). When the relative humidity is less than the predetermined threshold TH, summing the products of the temperature term $\gamma_T$, the humidity term $\gamma_{RH}$, and the step time term $\Delta t_i$ is omitted.

Figure 4:
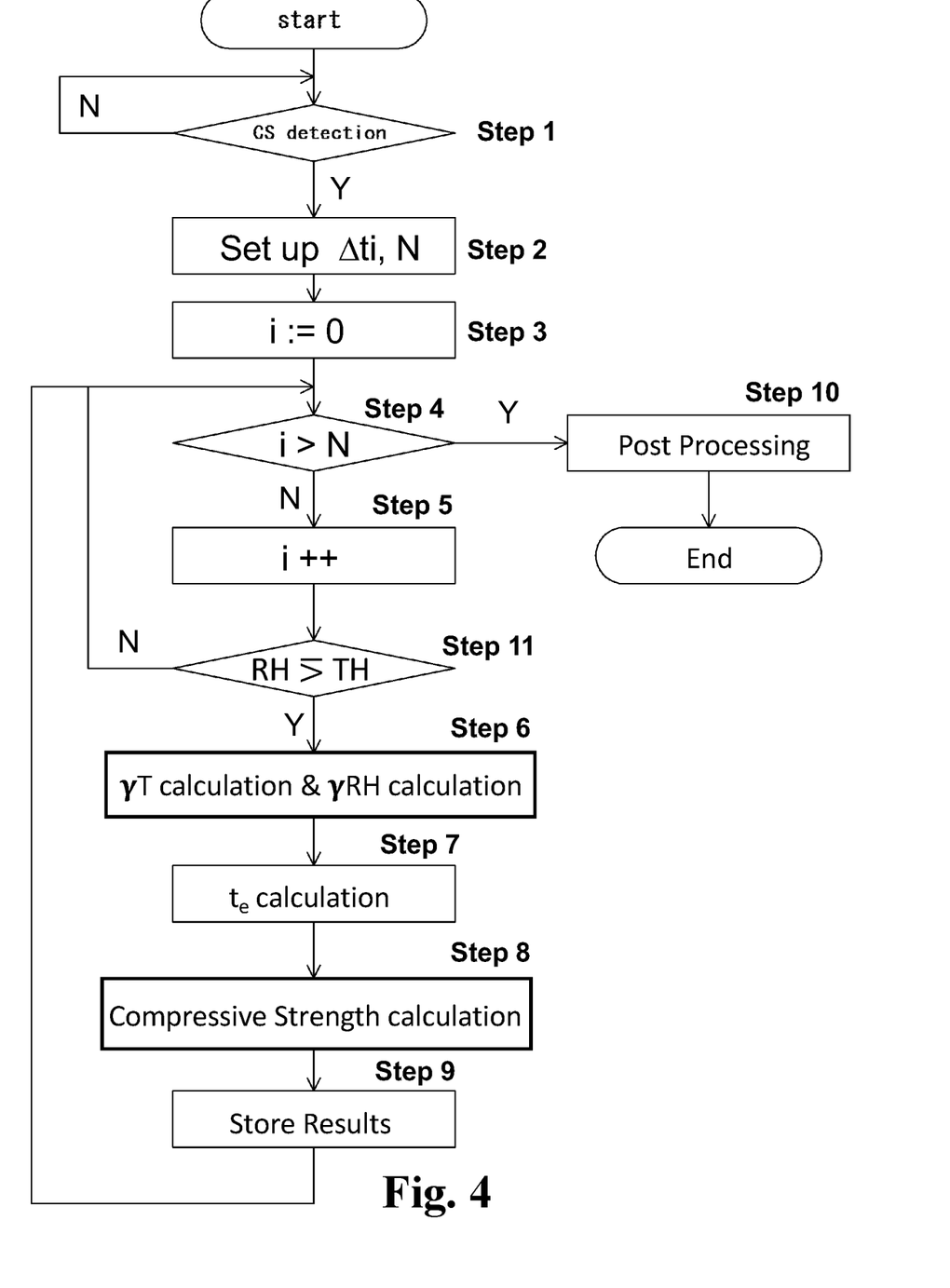
FIG. 4 is a flow chart of a compressive strength estimation device in Embodiment 2 according to the present invention.

More concretely as shown in FIG. 4, Step 11 is inserted between Step 5 and Step 6 of FIG. 3. At Step 11, the control unit 10 compares the relative humidity signals RH with the predetermined threshold TH. When the relative humidity signals RH are less than the predetermined threshold TH, the control unit 10 omits process from Step 6 to Step 9 to return the current process to Step 4.

When the products are summed and the value of summed products is zero or very close to zero, it may be said that the summing is not so useful. In Embodiment 2, process that is not so useful is omitted taking this point into consideration. This reasonable arrangement enables to save power consumption.

Points other than the above are similar to those in Embodiment 1.

Figure 5:
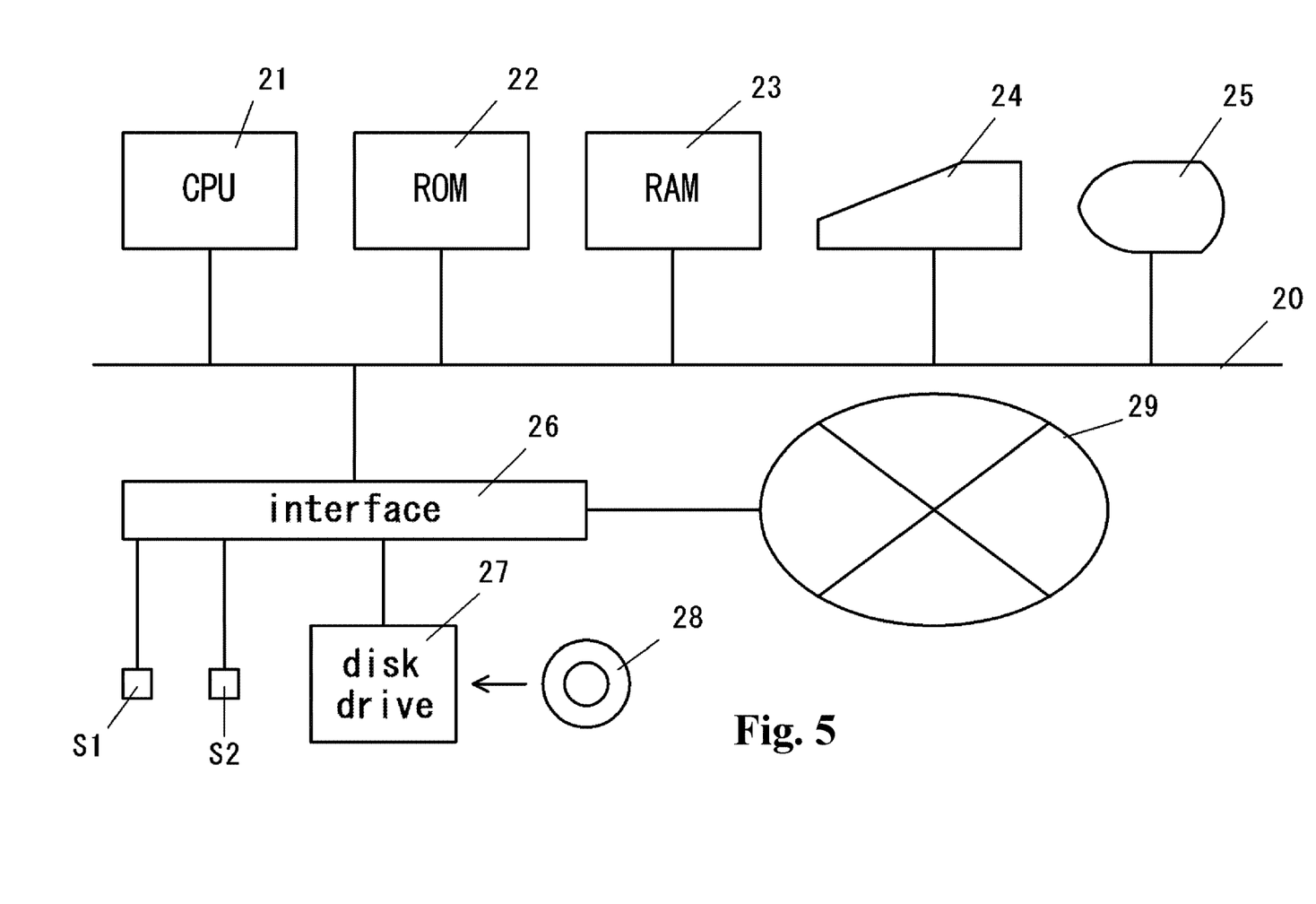
FIG. 5 is a block diagram showing a configuration example of the compressive strength estimation device in Embodiment 1 and Embodiment 2 according to the present invention.

FIG. 5 is a block diagram showing a configuration example of the compressive strength estimation device in Embodiment 1 and Embodiment 2 according to the present invention. In both of Embodiment 1 and Embodiment 2, the compressive strength estimation device can be configured as follows. Needless to say, the following description is a mere example, variation and/or modification can be applied thereto as long as obvious to those skilled in the art.

A CPU 21, a ROM 22, a RAM 23, a key board 24, and a display 25 are connected to a bus 20. Furthermore, the cast concrete detection sensor S1, the temperature/humidity sensor S2, a disk drive 27, and the Internet network 29 are connected to the bus 20 via an interface 26.

A recording medium 28 is detachably set onto a disk drive 28, and the recording medium 28 stores programs based on the flowcharts of FIG. 3 and/or FIG. 4.

The parameter storage unit 11 and the result storage unit 12 are implemented with the RAM 23. The CPU 21 executes programs stored onto the recording medium 28, thereby the control unit 10, the temperature calculation unit 13, the humidity calculation unit 13, the effective material age calculation unit 15, and the compressive strength calculation unit 16 are implemented, respectively.

BRIEF DESCRIPTION OF SYMBOLS 1, 2: Formwork
3: Concrete
10: Control unit
11: Parameter storage unit
12: Result storage unit
13: Temperature term calculation unit
14: Humidity term calculation unit
15: Effective material age calculation unit
16: Compressive strength calculation unit
20: Bus
21: CPU
22: ROM
23: RAM
24: Keyboard
25: Display
26: Interface
27: Disk drive
28: Recording medium
29: Internet network
S1: Cast concrete detection sensor
S2: Temperature/humidity sensor
D: Cast concrete detection signals
T: Temperature signals
RH: Relative humidity signals

The invention claimed is:

1. A device for estimating an effective age of a material, comprising:
a temperature term calculation unit for calculating a temperature term dependent on a temperature of a cast concrete;
a humidity term calculation unit for calculating a humidity term dependent on a relative humidity of the cast concrete;
an effective material age calculation unit for calculating an effective material age of the cast concrete by multiplying the temperature term, the humidity term, and a step time term, wherein the temperature term dependent on the temperature of T° C. is calculated in accordance with (Formula 1):

$$\gamma_T = \exp\left(13.65 - \frac{4000}{273 + T}\right).$$

wherein exp means an exponential function;
the humidity term $\gamma_{RH}$ dependent on the relative humidity of RH % is calculated in accordance with (Formula 2):

$$\gamma_{RH} = \exp\{-0.8484(100-RH)\}$$

wherein exp means an exponential function; and
the effective material age $t_e$ dependent on the step time term $\Delta t_i$ is calculated in accordance with (Formula 3):

$$t_e = \sum_i \Delta t_i \cdot \gamma_T \cdot \gamma_{RH},$$

wherein exp means an exponential function.

2. The device of claim 1, further comprising a temperature/humidity sensor for measuring the temperature of the cast concrete and the relative humidity of the cast concrete.

3. The device of claim 1, further comprising a cast concrete detection sensor for detecting a present or absence of the cast concrete.

4. The device of claim 1, wherein:
a predetermined threshold of the relative humidity is set up to be less than 100% and greater than 0%;
the humidity term reaches a positive maximum when the relative humidity is 100%;
the humidity term decreases within a first range wherein the relative humidity is less than 100% and not less than the predetermined threshold; and
the humidity term approaches asymptotically to 0% within a second range wherein the relative humidity is less than the predetermined threshold.

5. The device of claim 4, wherein the humidity term is set up to be zero within the second range.

6. The device of claim 4, wherein the predetermined threshold is set up to be a relative humidity from 80% to 95%.

7. The device of claim 1, wherein the effective material age calculation unit omits to sum the products of the temperature term, the humidity term, and the step time term when the relative humidity is less than the predetermined threshold.

8. A device for estimating a compressive strength, comprising:
the device of claim 1 for estimating the effective material age;
a compressive strength calculation unit operable to calculate a compressive strength of the cast concrete based on the effective material age $t_e$ calculated by the effective material age calculation unit of the effective material age estimation device defined in claim 1,
wherein the compressive strength $f_{ct}$ is calculated in accordance with at least one of the following Formula 4 and Formula 5;
Formula 4 dependent on the constant S, the setting time $t_s$, and the nominal strength $f_{c28}$ of the cast concrete is:

$$f_{Ct} = \exp\left\{s \cdot \left(1 - \sqrt{\frac{28}{t_e - t_s}}\right)\right\} \cdot f_{c28},$$

wherein exp means an exponential function, $t_s$ means setting time; and
Formula 5 dependent on the constants of "a" and "b" is:

$$f_{Ct} = \{t_e/(a+bt_e)\} \cdot f_{c28}.$$

* * * * *